(12) United States Patent
Glik et al.

(10) Patent No.: US 11,826,105 B2
(45) Date of Patent: Nov. 28, 2023

(54) RETINAL CAMERAS HAVING VARIABLY SIZED OPTICAL STOPS THAT ENABLE SELF-ALIGNMENT

(71) Applicant: Verily Life Sciences LLC, Mountain View, CA (US)

(72) Inventors: Eliezer Glik, San Francisco, CA (US); Honglei Wu, South San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 421 days.

(21) Appl. No.: 16/956,391

(22) PCT Filed: Dec. 17, 2018

(86) PCT No.: PCT/US2018/066024
§ 371 (c)(1),
(2) Date: Jun. 19, 2020

(87) PCT Pub. No.: WO2019/126046
PCT Pub. Date: Jun. 27, 2019

(65) Prior Publication Data
US 2022/0125309 A1    Apr. 28, 2022

Related U.S. Application Data

(60) Provisional application No. 62/609,149, filed on Dec. 21, 2017.

(51) Int. Cl.
*A61B 3/15*    (2006.01)
*A61B 3/00*    (2006.01)
*A61B 3/12*    (2006.01)

(52) U.S. Cl.
CPC ............ *A61B 3/152* (2013.01); *A61B 3/0008* (2013.01); *A61B 3/0058* (2013.01); *A61B 3/12* (2013.01); *A61B 3/15* (2013.01)

(58) Field of Classification Search
CPC ....... A61B 3/113; A61B 3/0091; A61B 3/152; G02B 5/005; A61F 2009/00846
(Continued)

(56) References Cited

U.S. PATENT DOCUMENTS 4,743,107 A    5/1988  Aizu et al.
4,834,526 A *  5/1989  Nunokawa ............... A61B 3/14
                                                            396/18
(Continued)

FOREIGN PATENT DOCUMENTS

WO    2007127157 A3    4/2008

OTHER PUBLICATIONS

International Search Report and Written Opinion dated Apr. 25, 2019 for PCT Application No. PCT/US2018/066024, filed Dec. 17, 2018., dated Apr. 25, 2019, 7 pages.

*Primary Examiner* — Zachary W Wilkes
(74) *Attorney, Agent, or Firm* — Perkins Coie LLP

(57) ABSTRACT

Introduced here are retinal cameras having optical stops whose size can be adjusted to enable self-alignment by naturally guiding an eye toward a specified location. Generally, a retinal camera will constrict the bounds of an optical stop until the optical stop is aligned with the eye. In some embodiments, the optical stop is mechanically resized as a subject shifts their eye. In some embodiments, the optical stop is digitally created using a pixelated liquid crystal display (LCD) layer having multiple pixels that are individually controllably. In some embodiments, multiple non-pixelated LCD layers are connected to one another to form a variable transmission stack. In such embodiments, the size of the optical stop can be varied by changing which LCD layer(s) are active at a given point in time.

15 Claims, 12 Drawing Sheets

(58) Field of Classification Search
USPC .......................................... 351/209, 214, 208
See application file for complete search history.

(56) References Cited

U.S. PATENT DOCUMENTS

| | | | | |
|---|---|---|---|---|
| 6,546,198 | B2 * | 4/2003 | Ohtsuka | A61B 3/12 |
| | | | | 396/18 |
| 7,025,459 | B2 * | 4/2006 | Cornsweet | A61B 3/156 |
| | | | | 351/200 |
| 7,241,011 | B2 | 7/2007 | Baek et al. | |
| 7,907,336 | B2 * | 3/2011 | Abele | A61B 3/13 |
| | | | | 359/385 |
| 9,254,084 | B2 * | 2/2016 | Yoshino | A61B 3/12 |
| 10,027,899 | B2 * | 7/2018 | He | G02B 26/04 |
| 10,420,464 | B2 * | 9/2019 | Wilf | G02B 27/1066 |
| 10,437,327 | B2 * | 10/2019 | Sengelaub | A61B 3/113 |
| 10,492,681 | B2 * | 12/2019 | Nozato | A61B 3/1015 |
| 10,849,498 | B2 * | 12/2020 | Tumlinson | A61B 3/12 |
| 2007/0030450 | A1 | 2/2007 | Liang et al. | |
| 2008/0100801 | A1 * | 5/2008 | Yahagi | A61B 3/12 |
| | | | | 351/206 |
| 2008/0304012 | A1 | 12/2008 | Kwon et al. | |
| 2013/0033593 | A1 | 2/2013 | Chinnock et al. | |
| 2016/0038024 | A1 * | 2/2016 | Zhou | A61B 3/113 |
| | | | | 351/206 |
| 2016/0143528 | A1 * | 5/2016 | Wilf | A61B 3/14 |
| | | | | 351/246 |

* cited by examiner

900

901
Subject places eye proximate to the objective lens of a retinal camera

902
Determine the location of the eye to be imaged by the retinal camera

903
Configure an optical stop to be a first size

904
Monitor the position of the eye

905
Adjust the optical stop to be a second size responsive to determining that the position of the eye has changed 906
Generate retinal image from light rays reflected into retinal camera by the eye

FIGURE 9

RETINAL CAMERAS HAVING VARIABLY SIZED OPTICAL STOPS THAT ENABLE SELF-ALIGNMENT

CROSS-REFERENCE TO RELATED APPLICATIONS

This application is a U.S. National Phase Patent Application of International Patent Application No. PCT/US2018/066024, filed on Dec. 17, 2018, which claims priority to U.S. Provisional Application No. 62/609,149, titled "Retinal Cameras Having Variably Sized Optical Stops That Enable Self-Alignment" and filed on Dec. 21, 2017, each of which is incorporated by reference herein in its entirety.

TECHNICAL FIELD

Various embodiments concern retinal cameras having optical stops.

BACKGROUND

Fundus photography involves capturing an image of the fundus (i.e., the interior surface of the eye opposite the lens) to document the retina, which is the neurosensory tissue in the eye that translates optical images into the electrical impulses that can be understood by the brain. The fundus can include the retina, optic disc, macula, fovea, and posterior pole.

Retinal cameras (also referred to as "fundus cameras") typically include a microscope and a capturing medium that creates an image from light reflected by the retina. Because the pupil serves as both the entrance point and exit point of light guided toward the retina, the retina can be photographed directly. The structural features that can be identified on a retinal photograph include the central and peripheral retina, optic disc, and macula.

Medical professionals (e.g., optometrists, ophthalmologists, and orthoptists) can use retinal images to monitor the progression of certain diseases and eye conditions. For example, retinal images may be used to document indicators of diabetes, age-macular degeneration (AMD), glaucoma, neoplasm, etc.

BRIEF DESCRIPTION OF THE DRAWINGS

Various characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 9 depicts a flow diagram of a process for dynamically modifying the size of an optical stop housed within a retinal camera as a subject shifts their eye before the imaging process.

Figure 1:
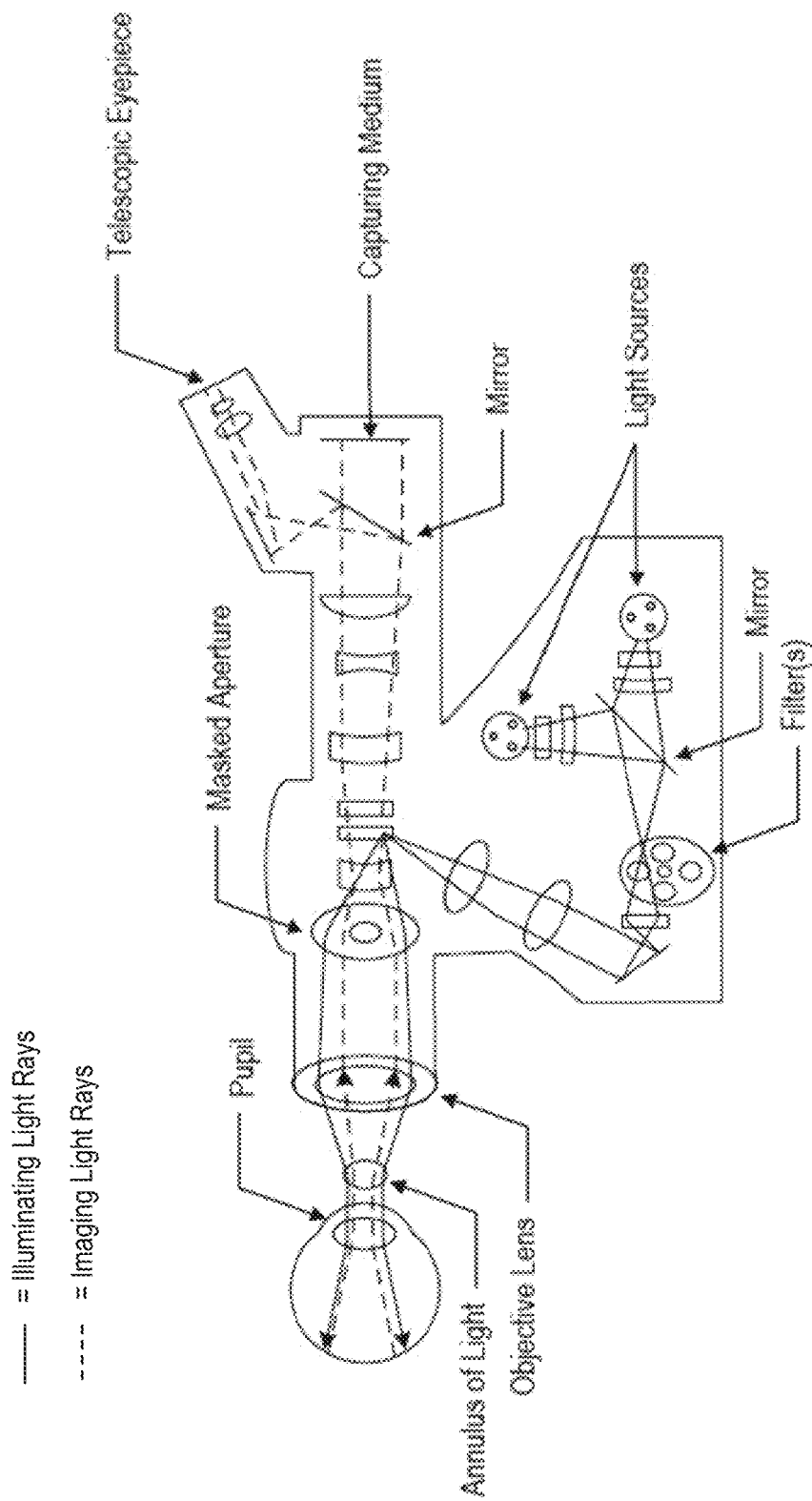
FIG. 1 depicts an example of a retinal camera.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Retinal cameras are designed to provide an upright, magnified view of the fundus. Typically, a retinal camera views 30-50° of the retinal area with a magnification of 2.5×, though these values may be modified using zoom lenses, auxiliary lenses, wide angle lenses, etc.

FIG. 1 depicts an example of a retinal camera. Generally, a subject will sit at the retinal camera with their chin set within a chin rest and their forehead pressed against a bar. An ophthalmic photographer can then visually align the retinal camera (e.g., using a telescopic eyepiece) and press a shutter release that causes an image of the retina to be captured.

More specifically, FIG. 1 illustrates how light can be focused via a series of lenses through a masked aperture to form an annulus that passes through an objective lens and onto the retina. The illuminating light rays are generated by one or more light sources (e.g., light-emitting diodes), each of which is electrically coupled to a power source. When the retina and the objective lens are aligned, light reflected by the retina passes through the un-illuminated hole in the annulus formed by the masked aperture of the retinal camera. Those skilled in the art will recognize that the optics of the retinal camera are similar to those of an indirect ophthalmoscope in that the illuminating light rays entering the eye and the imaging light rays exiting the eye follow dissimilar paths.

The imaging light rays exiting the eye can initially be guided toward a telescopic eyepiece that is used by the ophthalmic photographer to assist in aligning, focusing, etc., the illuminating light rays. When the ophthalmic photographer presses the shutter release, a first mirror can interrupt the path of the illuminating light rays and a second mirror can fall in front of the telescopic eyepiece, which causes the imaging light rays to be redirected onto a capturing medium. Examples of capturing mediums include film, digital charge-coupled devices (CODs), and complementary metal-oxide-semiconductors (CMOSs). In some embodiments, retinal images are captured using colored filters or specialized dyes (e.g., fluorescein or indocyanine green).

Accordingly, stable alignment of the eye and the retinal camera is critical in capturing high-resolution retinal images. However, initiating such an alignment in preparation for an imaging process can be challenging due to the required precision, and then maintaining such an alignment throughout the imaging process can be challenging due to the lack of direct eye gaze control.

Introduced here, therefore, are retinal cameras having optical stops whose size and/or position can be modified to increase the size of the space in which an eye can move while being imaged (also referred to as the "eyebox"). More specifically, variably sized optical stops can enable self-alignment by naturally guiding the eye toward a specified location (e.g., the epicenter of an optical stop). The term "optical stop" refers to the location where light rays entering a retinal camera are traced. Because a retinal camera images light rays reflected back into the retinal camera by the retina, the optical stop is arranged along a plane located inside the retinal camera.

Figure 2:
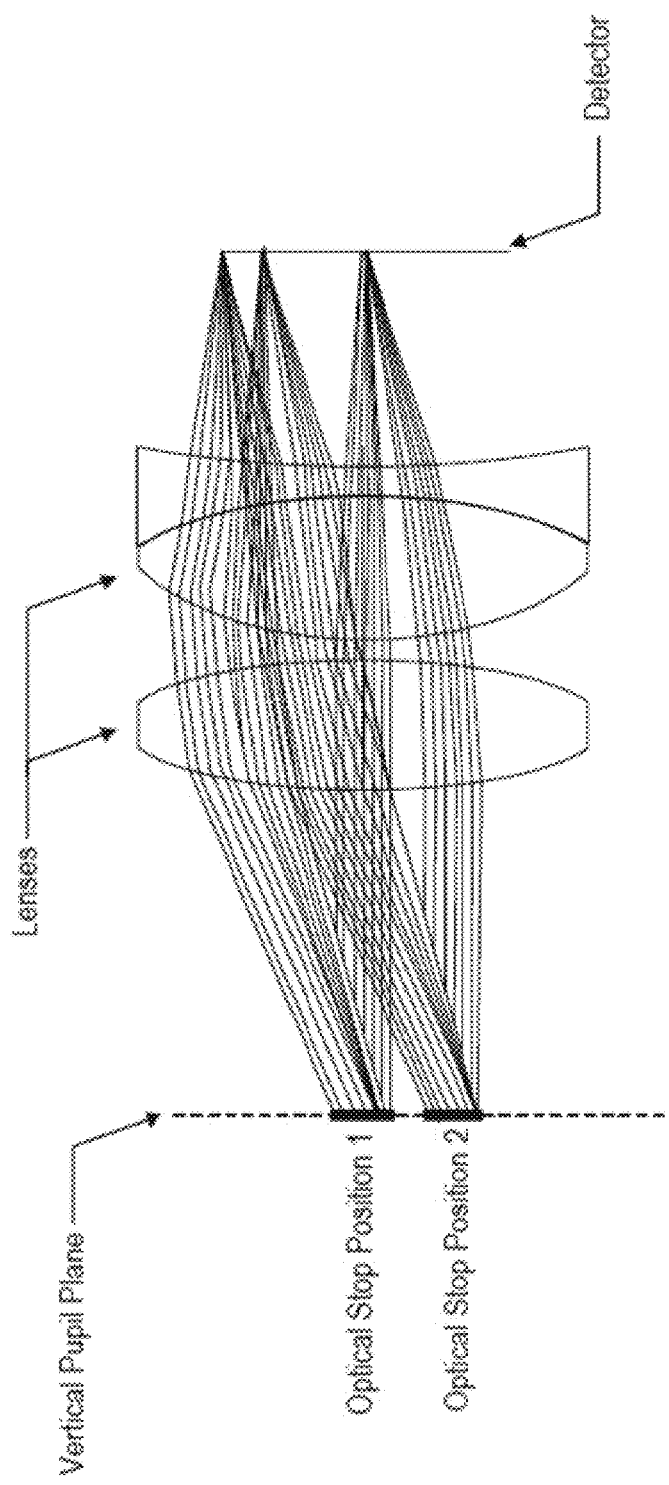
FIG. 2 depicts how moving the eye vertically along the pupil plane may only change the angle of incidence (AOI) of the light rays to the detector of certain eyepieces.

This stands in contrast to other types of eyepieces (e.g., head-mounted devices) where the eye (and, more specifically, the iris) represents the optical stop. For these eyepieces, altering the position of the optical stop does not cause displacement of the light rays along a detector. FIG. 2 depicts how moving the eye vertically along the pupil plane may only change the angle of incidence (AOI) of the light rays to the detector. Here, the first optical stop position represents the optimal eye location (i.e., where the image of the highest quality would be captured) and the second optical stop position represents another position within the eyebox. Because the eye itself acts as the optical stop, a subject can move their eye between the first and second positions without causing vertical or horizontal displacement of the light rays along the detector.

These other types of eyepieces allow for a certain eyebox by having optical stop(s) that are larger than the iris. For example, the entrance pupil is usually larger than the iris to allow easy alignment between the two. If the iris fits within the bounds of the entrance pupil, then an image presented by the eyepiece will be fully visible.

Retinal cameras often include multiple optical stops that must be aligned with the iris in order for the eye to be properly illuminated, imaged, etc. However, alignment can be difficult because the iris may need to be precisely aligned with each of the multiple optical stops (e.g., an illumination pupil, imaging pupil, and microdisplay pupil). To maximize the quality of images of the eye, two criteria must generally be satisfied. First, all of these optical stops may be aligned with the iris. Second, at least some of these optical stops may be of similar size as the iris.

Conventional retinal cameras include optical stops of a predetermined size. When these optical stops are roughly the same size as the iris after accounting for magnification, the optical stops are capable of capturing high-quality images but they are difficult to quickly discover with the eye. This is why alignment is often manually performed by a trained operator.

The retinal cameras described here, however, can include variably sized optical stops that enable self-alignment. An optical stop can initially be configured to be a specified size. For example, the optical stop may initially be larger than the iris (e.g., 2×, 3×, or 5× larger than the iris). The position of the eye can then be continually monitored in real time, and the size of the optical stop can be dynamically varied in response to detecting spatial adjustments of the eye.

For example, as the location of the eye approaches a specified location, the bounds of the optical stop can constrict to guide the eye toward the specified location. As another example, as the location of the eye diverges from the specified location, the bounds of the optical stop can expand. The specified location may substantially align with the epicenter of the optical stop. Thus, the optical stop may be configured to shrink until the iris is properly aligned with the epicenter of the optical stop, the full field-of-view (FOV) is viewable, and the optical stop is the appropriate size (e.g., roughly the same diameter as the iris after accounting for magnification).

Embodiments may be described with reference to particular imaging configurations, eyepieces, etc. However, those skilled in the art will recognize that the features described herein are equally applicable to other imaging configurations, eyepieces, etc. Moreover, the technology can be embodied using special-purpose hardware (e.g., circuitry), programmable circuitry appropriately programmed with software and/or firmware, or a combination of special purpose hardware and programmable circuitry. Accordingly, embodiments may include a machine-readable medium having instructions that may be used to program a computing device to perform a process for tracking the position of an eye, modifying the size of an optical stop, processing image data to generate a retinal photograph, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling, either direct or indirect, between two or more elements. The coupling/connection can be physical, logical, or a combination thereof. For example, components may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

Alignment is one of the most difficult tasks of retinal imaging. Conventional retinal cameras, for instance, typically require a trained operator, proper securement of the head position, and non-trivial mechanical controls to ensure precise alignment of the eye and imaging components within the retinal camera (e.g., the lenses, optical stop, and detector). Consequently, the eyebox dimensions of conventional retinal cameras are often extremely limited. This makes proper alignment of the eye and the retinal camera difficult, particularly if the subject begins to shift their eye before or during the imaging process.

Several solutions have been proposed to address the problems posed by small eyeboxes. However, these proposed solutions add mechanical complexity to the retinal camera (and thus increase the cost). Introduced here, therefore, are several different technologies for dynamically adjusting the size of an optical stop to facilitate self-alignment prior to initiation of the imaging process, including:

A mechanical optical stop whose size can be varied as the subject shifts their eye. For example, a mechanical optical stop may include multiple blades that, upon being rotated, can increase/decrease the size of the mechanical optical stop. In some embodiments the blades automatically rotate based on the location of the eye, while in other embodiments the blades rotate based on input manually provided by a trained operator (e.g., by turning a knob).

A digital optical stop that can be created using a pixelated liquid crystal display (LCD) layer including multiple pixels that are individually controllable.

Multiple non-pixelated LCD layers that can be connected to one another to form a stack. Each LCD layer within the stack may be offset from the other LCD layers. Accordingly, the size of the optical stop of the retinal camera can be varied by changing how many LCD layers are active at a given point in time. Alternatively, if the LCD layers are of different sizes, then the size of the optical stop of the retinal camera can be varied by changing which LCD layer is active at a given point in time.

Each of these technologies is further described below.

Figure 3:
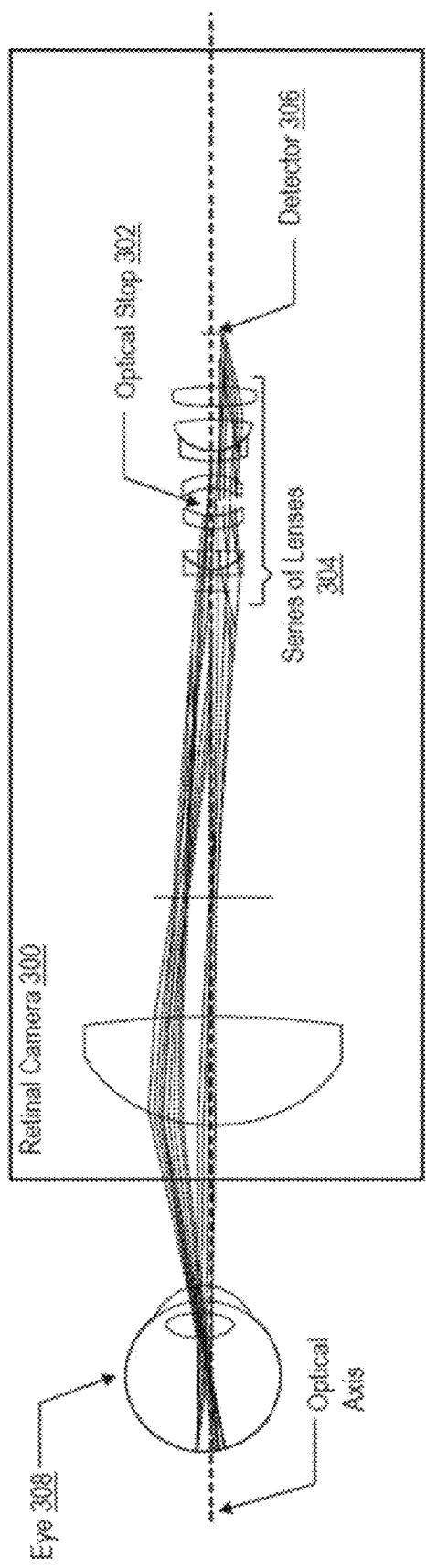
FIG. 3 illustrates a generalized side view of a retinal camera.

FIG. 3 illustrates a generalized side view of a retinal camera 300. Here, the retinal camera 300 includes an optical stop 302 interposed between a series of lenses 304 and a detector 306 (also referred to as a "capturing medium"). Generally, the detector 306 is arranged directly adjacent to the series of lenses 304. Other embodiments of the retinal camera 300 may include some or all of these components, as well as other components not shown here. For example, the retinal camera may include one or more light sources, mirrors for guiding light emitted by the light source(s), a power component (e.g., a battery or a mechanical power interface, such as an electrical plug), a display screen for reviewing retinal images, etc.

As noted above, in some embodiments the size of the optical stop 302 can be adjusted to facilitate stabilization of the eye 308 through natural vignetting. More specifically, the eye 308 may initially be able to observe an image produced by the retinal camera 300 through the optical stop 302 configured to be a specified size. Generally, the specified size is larger than the iris (e.g., 2×, 3×, or 5× larger than the iris). Although such action will ensure that the eye 308 can easily fit within the eyebox, large optical stops are not capable of capturing high-quality images.

Accordingly, the position of the eye 308 may be continually monitored in real time, and the size of the optical stop 302 can be dynamically varied in response to detecting spatial adjustments of the eye 308. For example, as the eye 308 moves toward a specified location, the bounds of the optical stop 302 can constrict. As another example, as the eye moves away from the specified location, the bounds of the optical stop 302 can expand. In some embodiments, the specified location may be the epicenter of the optical stop 302. In other embodiments, the optical stop 302 simply continues to shrink until the optical stop 302 is roughly the same diameter of the iris and precisely aligned with the iris (e.g., within 0.05 or 0.1 millimeters). In such embodiments, the optical stop 302 may not be designed to guide the eye 308 toward a predefined location.

Stabilization of the eye 308 can be facilitated by the natural vignetting of an image visible through the retinal camera 300. As noted above, the eye 308 may initially be able to observe an image produced by the retinal camera 300. However, because the optical stop 302 is initially larger than the iris, the quality of the image will be poor. For example, resolution of the image may be poor around the periphery of the image. Other characteristics may also affect quality such as vignetting, brightness, etc.

Generally, the poor quality around the periphery of the image will naturally cause the eye 308 to shift toward the highest quality portion of the image. Such action cause the iris to move within the bounds of the optical stop 302, and the bounds of the optical stop 302 can begin shrinking until substantially matching the bounds of the iris. Thus, the optical stop 302 can promote self-alignment in a natural way. When the size of the optical stop 302 is similar to the size of the iris, substantially all of the imaging light rays returning from the eye 308 (e.g., the imaging light rays of FIG. 1) can be guided through the series of lenses 304 and captured by the detector 306.

The eye 308 can also be guided toward a specified location in other ways. For example, the retinal camera 300 may present an active signal on a display (not shown) visible to the eye 308. Examples of active signals include arrows, targets, and other graphical representations likely to attract the attention of the eye 308. The size of the optical stop 302 may also vary in response to random movements of the eye 308 (e.g., movements not prompted by the retinal camera 300).

The relationship between eye shift and optical stop size changes may be substantially linear (e.g., approximately one-to-one). Such a relationship allows the proper size of the optical stop 302 to be readily established so long as the position of the eye 308 can be accurately established.

In some embodiments, the size of the optical stop 302 is modified manually. For example, a retinal photographer may visually observe the imaging light rays (e.g., via a telescopic eyepiece) during an imaging session and alter the size of the optical stop 302 using indexing wheel(s), joystick(s), etc.

In other embodiments, the size of the optical stop 302 is modified automatically without requiring input from the retinal photographer or the subject. The retinal camera 300 may instruct servomotor(s) to alter the size of the optical stop 302 responsive to adjustments specified by software executing on the retinal camera 300 or another computing device communicatively coupled to the retinal camera 300. Separate servomotors may be used to alter the position of various mechanical components. For example, servomotor(s) may be responsible for causing multiple blades to rotate, thereby increasing/decreasing the size of the optical stop. As another example, servomotor(s) may be responsible for moving mechanical plate(s) along the x-axis (i.e., horizontally) and/or the y-axis (i.e., vertically). Other mechanisms may also be used to vary the size of the optical stop 302, including cam(s), stepper motor(s), pneumatic cylinder(s)/actuator(s), piezoelectric actuator(s), voice coil(s), etc.

In some embodiments, movement occurs along a single dimension. For example, the size of the optical stop 302 may be controllably increased/decreased by rotating multiple blades that work together to define the bounds of the optical stop. In other embodiments, movement occurs along multiple dimensions. For example, the multiple blades may also be configured to move along a path (e.g., a circular/ellipsoidal path, a rectangular path, or a spiral path) to increase/decrease the distance between the eye 308 and the optical stop 302.

The software may also apply image processing algorithms to identify certain features (e.g., vignetting) that are indicative of increases/decreases in retinal image quality. For example, the software may perform image segmentation (e.g., thresholding methods such as Otsu's method, or color-based segmentation such as K-means clustering) on individual retinal images to isolate features of interest. After the software has identified the retinal image having the highest quality, the software can output instructions that cause the servomotor(s) to modify the size of the optical stop 302. Similarly, the software can output instructions that specify where the epicenter of the optical stop 302 should be located.

Image quality can depend on one or more factors, such as brightness level, whether vignetting is present, modulation transfer function (MTF) quality, etc. The optical transfer function (OTF) of an optical system (e.g., a retinal camera) specifies how different spatial frequencies are handled by the optical system. A variant, the MTF, neglects phase effects but is otherwise equivalent to the OTF in many instances.

Thus, a subject may be able to look into the retinal camera 300 without being concerned about aligning the eye 308 and the optical stop 302. Instead, the retinal camera 300 could automatically begin decreasing the size of the optical stop 302 until the optical stop 302 is roughly the same size as the iris. The retinal camera 300 may include a mechanism (e.g., a servomotor) operable to modify the size of the optical stop 302 and/or a controller configured to adaptively vary the size of the optical stop 302 responsive to a determination that the eye 308 has moved. Generally, the size of the optical stop 302 is dynamically varied prior to the imaging process. However, such action may also occur during the imaging process.

More specifically, the controller may determine the amount of movement caused by a spatial adjustment of the eye 308, and then cause the mechanism to resize the optical stop 302 accordingly. As noted above, the amount of movement caused by the spatial adjustment of the eye 308 may be related (e.g., proportional to) the amount by which the size of the optical stop 302 is adjusted. Thus, the size of the optical stop 302 could be adjusted to ensure the optical stop 302 is roughly the same size as the iris and aligns with the iris, rather than moving the entire retinal camera 300 or the eye 308 itself. In some embodiments, optimized adjustments also occur based on, for example, an image quality feedback loop or some other feedback loop.

Several different mechanisms can be used to detect the location of the eye 308. For example, infrared light source(s) may be arranged to project infrared beam(s) into the visible light illumination path of the retinal camera 300. Because the iris generally does not constrict when illuminated by infrared light, a live view (e.g., a live video view) of the retina can be captured and used to establish the position of the eye 308. As another example, the iris may be detected using a software-implemented search pattern. More specifically, the retinal camera 300 could capture a series of retinal images with the optical stop 302 located at different positions. The ideal position for the optical stop 302 may be determined based on whether the retina is detected within any of the retinal images. Other mechanisms for detecting eye location include conventional eye tracking techniques, pupil discover via machine vision, Light Detection and Ranging (LIDAR), radio frequency (RF) object sensing at certain frequencies (e.g., 60 GHz), simple reflection off the cornea, etc.

In some embodiments, the retinal camera 300 includes one or more components that are not shown here. For example, the retinal camera 300 may include a beam splitter configured to split incoming light before the imaging plane. In such embodiments, the beam splitter may direct a portion of the incoming light toward the detector 306 and another portion of the incoming light toward a display (e.g., a micro-display of similar size as the detector 306).

Figure 4:
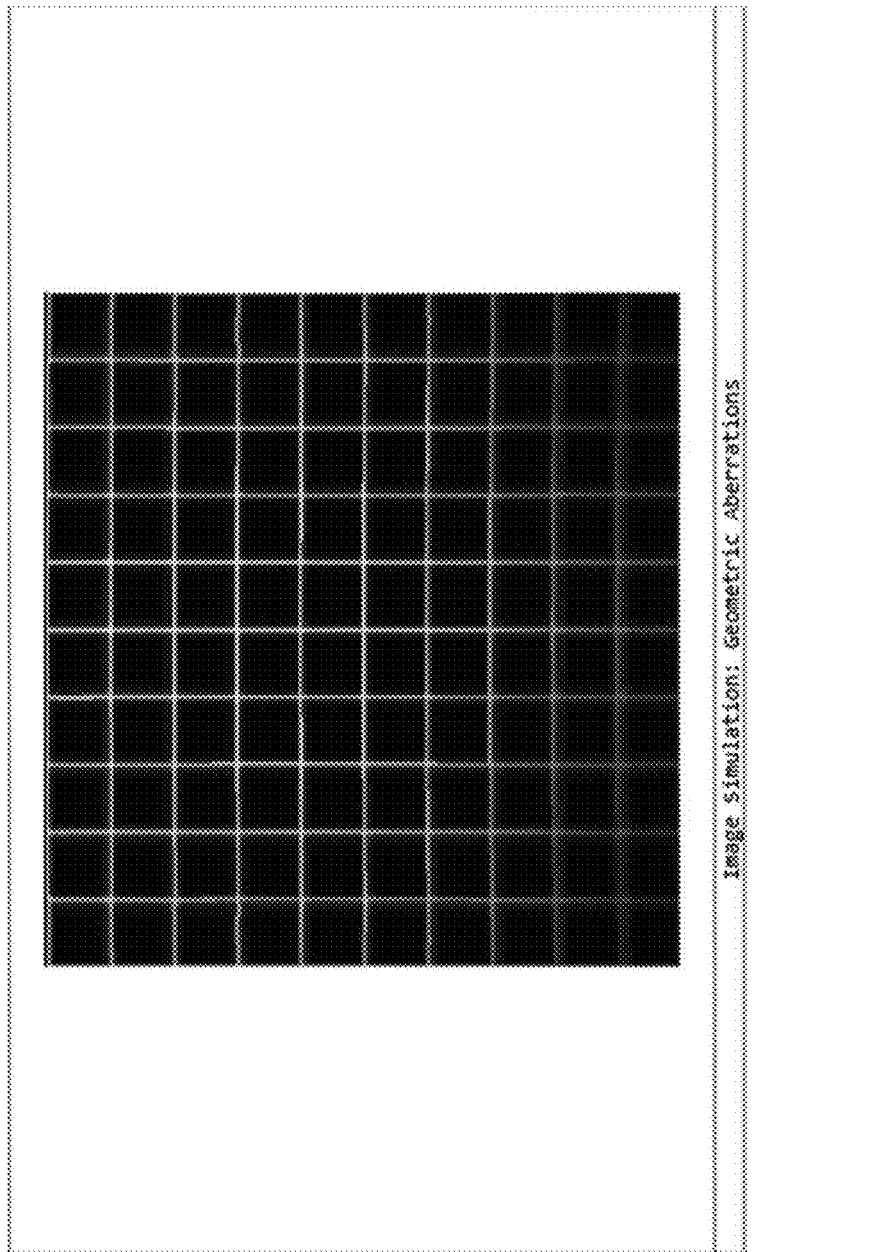
FIG. 4 depicts an example of an image that may be visible to the patient through a retinal camera.

Small shifts in the position of the eye can create noticeable changes in image quality. FIG. 4 depicts an example of an image that may be visible through a retinal camera. Stabilization of the eye viewing the image can be facilitated by vignetting present when the optical stop of the retinal camera is larger than the iris. Vignetting generally refers to the reduction of brightness or saturation at the periphery compared to the center of the image. Vignetting is apparent in the changes to the colors and contrast along the periphery of the image. Here, for example, the top of the image has high resolution and contrast, while the bottom of the image suffers from poor resolution and contrast.

Figure 5A:
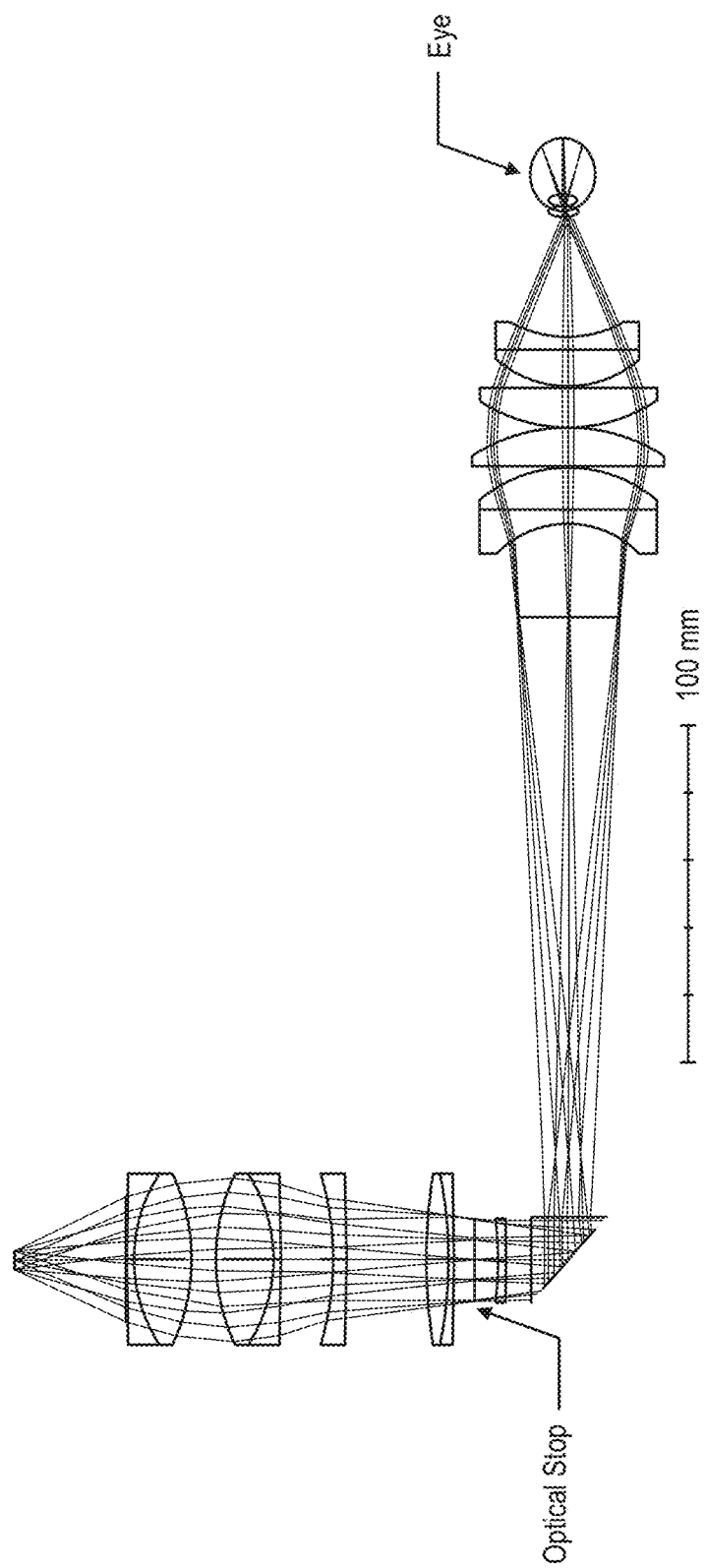
FIG. 5A depicts an example of a retinal camera that includes an optical stop that is larger than the iris.

FIG. 5A depicts an example of a retinal camera that includes an optical stop that is larger than the iris. Although the eye is misaligned with the optical stop, the eye will still observe the full FOV. However, the eye will naturally attempt to align itself with the epicenter of the optical stop so that the FOV includes the portion of the image having the best quality (e.g., the highest resolution or contrast). The size of the optical stop can be dynamically adjusted as such alignment occurs.

Figure 5B:
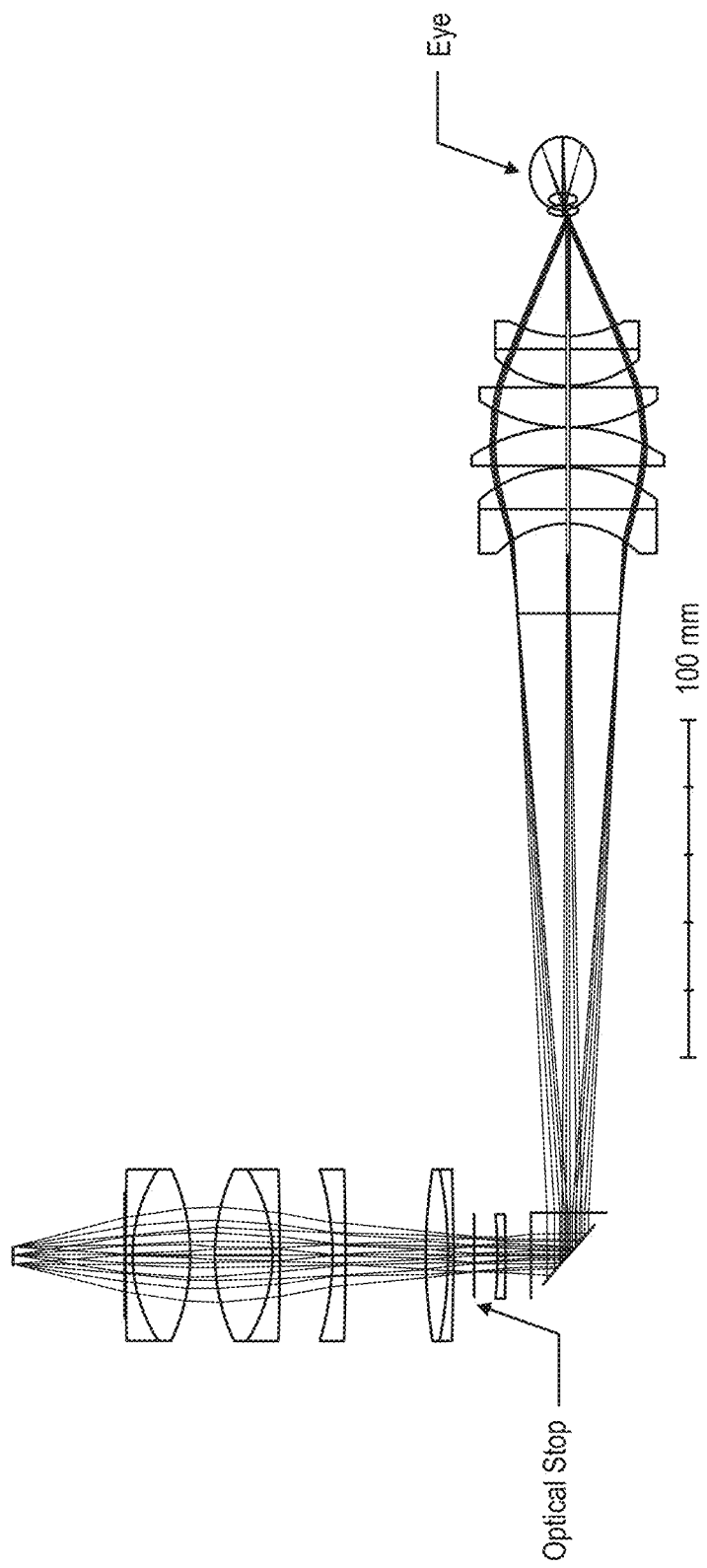
FIG. 5B depicts an example of a retinal camera that includes an optical stop that is smaller than the iris.

FIG. 5B depicts an example of a retinal camera that includes an optical stop that is misaligned with the iris. Misalignment may occur when the iris and the optical stop only partially overlap one another. In such a scenario, the subject will be unable to observe the full FOV. This can occur if the size of the optical stop is decreased and the optical stop is not aligned with the iris. If the subject is able to see the entire FOV during the previous step, then they will likely position the eye so that it can see the FOV again.

Figure 5C:
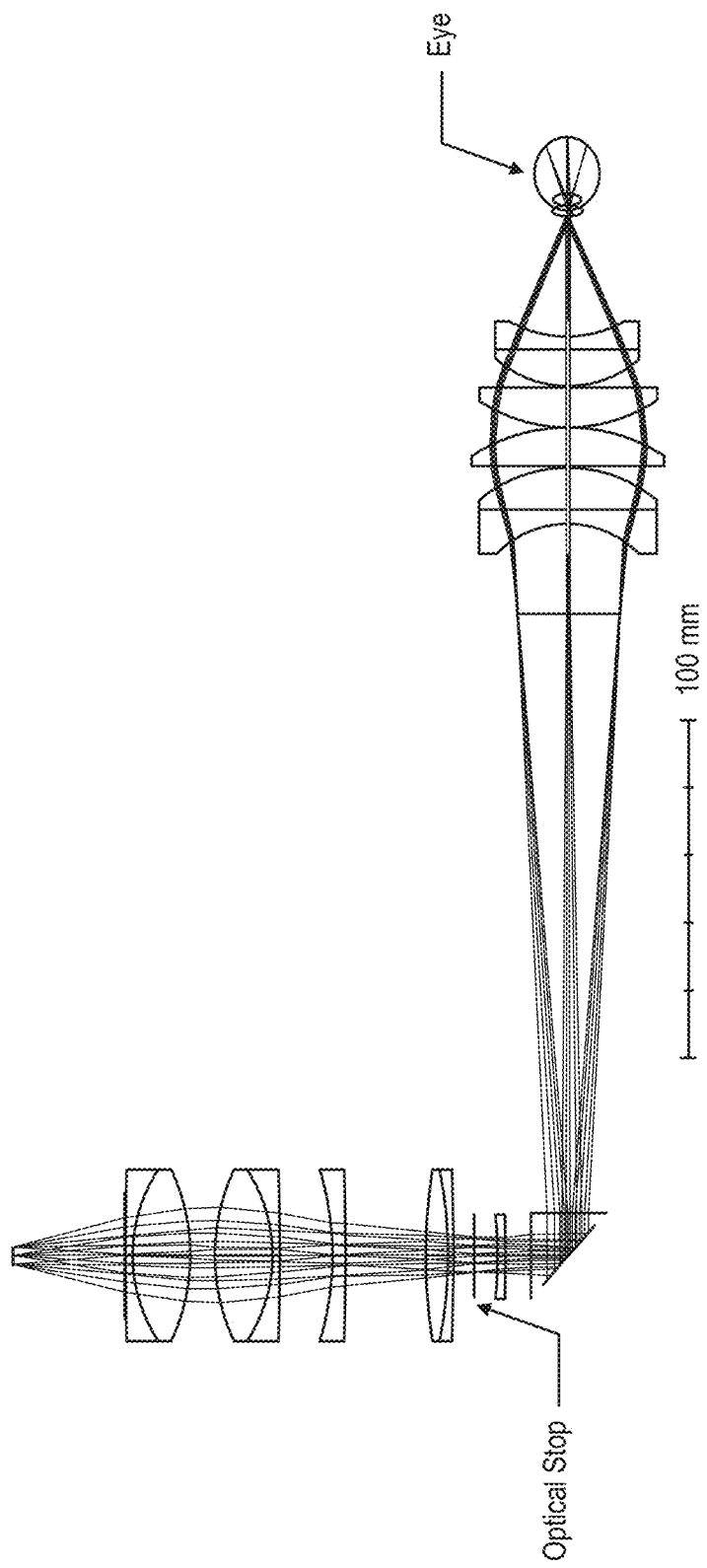
FIG. 5C depicts an example of a retinal camera that includes an optical stop that is roughly equivalent in size to the iris and aligned with the iris.

FIG. 5C, meanwhile, depicts an example of a retinal camera that includes an optical stop that is roughly equivalent in size to the iris and aligned with the iris. Proper alignment may require that the bounds of the optical stop substantially match the bounds of the iris, and thus the epicenter of the optical stop may substantially align with the epicenter of the iris.

Figure 6:
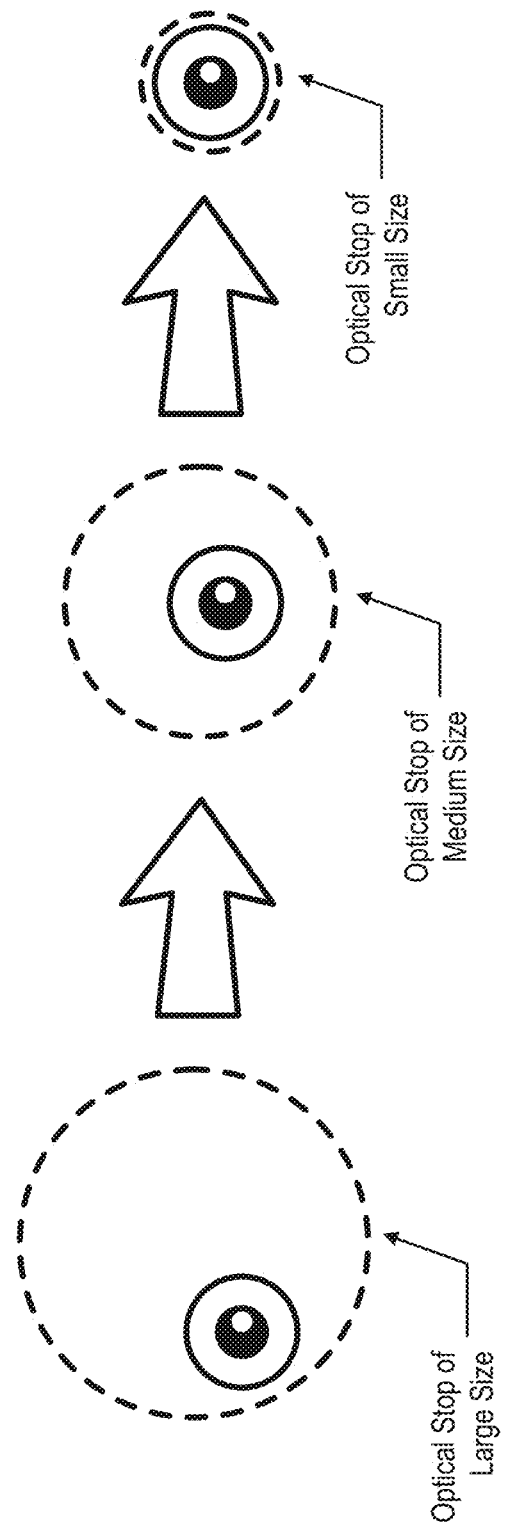
FIG. 6 illustrates how the size of an optical stop can be dynamically adjusted as an eye aligns itself with the epicenter of the optical stop.

FIG. 6 illustrates how the size of an optical stop can be dynamically adjusted as an eye aligns itself with the epicenter of the optical stop. The optical stop may initially be configured to be a specified size. For example, the optical stop can initially be set to a maximum size allowed by a retinal camera to ensure that the eye is in the eyebox.

The position of the eye can then be continually monitored in real time. Moreover, the size of the optical stop can be dynamically varied in response to detecting spatial adjustments of the eye. Here, for example, the bounds of the optical stop constrict as the eye stabilizes on an image being shown by a retinal camera. Said another way, the bounds of the optical stop can constrict as the eye approaches a specified location. In some embodiments, the bounds of the optical stop may also expand as the eye diverges from the specified location. The optical stop may be configured to shrink until the optical stop is roughly the same diameter as the iris, and until the epicenter of the optical stop is substantially aligned with the epicenter of the iris.

Figure 7:
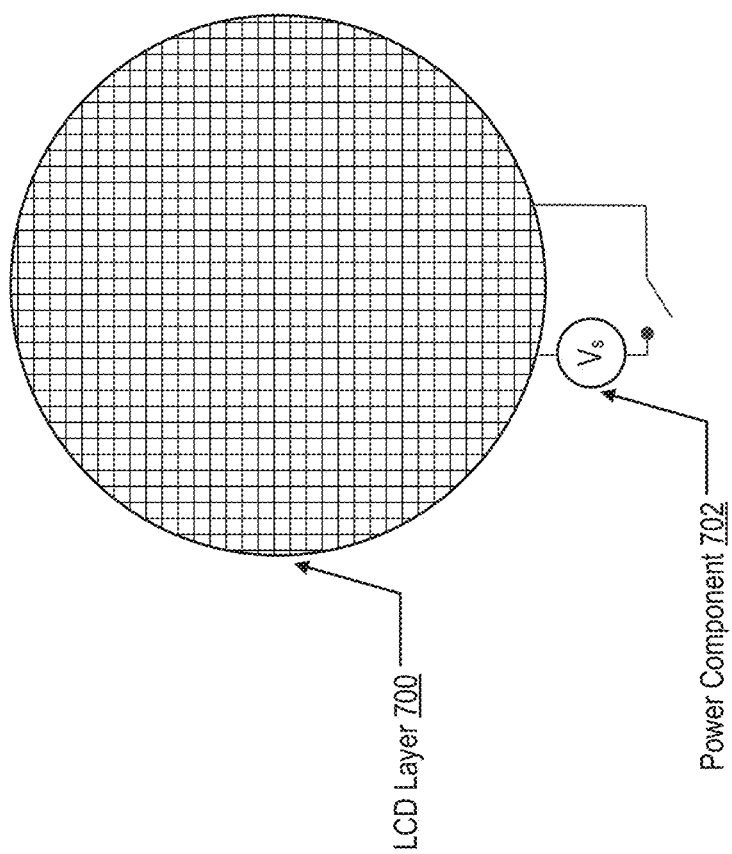
FIG. 7 depicts a pixelated liquid crystal display (LCD) layer having multiple pixels that are individually controllable.

FIG. 7 depicts a pixelated liquid crystal display (LCD) layer 700 having multiple pixels that are individually controllable. The LCD layer 700 may be electrically coupled to a power component 702 that is able to separately apply a voltage to each pixel to vary its transparency. Provisioning voltage in such a manner allows the power component 702 to digitally create an optical stop by changing which pixel(s) in the LCD layer 700 are active at a given point in time. Such action can be facilitated by one or more polarizing layers (also referred to as "polarizers") arranged within, or adjacent to, the LCD layer 700.

Changing the transparency of a pixel will allow light to pass through the corresponding segment of the LCD layer 700. For example, a segment of the LCD layer 700 that includes one or more pixels may appear substantially transparent when used as an optical stop. The remainder of the LCD layer 700 may appear partially or entirely opaque. To modify the size of the optical stop, the power component 702 may apply voltage(s) causing substantially transparent pixels to become substantially opaque and/or causing substantially opaque pixels to become substantially transparent.

Here, the LCD layer 700 is illustrated as a circle. However, those skilled in the art will recognize that the outer bounds of the LCD layer 700 could form another geometric shape. For example, other shapes (e.g., a square, rectangle, or ellipsoid) may be preferred based on the configuration of the retinal camera, the expected movement of the eye, the design of the digitally-created optical stop, etc.

Moreover, the LCD layer 700 could include any number of pixels. In some embodiments, the LCD layer 700 includes tens or hundreds of pixels. In such embodiments, the optical stop may be defined by multiple pixels (e.g., an optical stop can vary in size from an eight-by-eight pixel segment to a four-by-four pixel segment). In other embodiments, the LCD layer 700 includes fewer pixels, though those pixels are often larger in size. For example, the LCD layer 700 may include four, six, or eight separately-controlled pixels.

Note that other forms of pixelated display technologies may also be used, such as plasma display panels (PDPs) and electronic ink displays. Thus, the LCD layer 700 could instead be a "variable transparency layer" able to alter its appearance in several different ways. Moreover, because these pixelated display technologies often absorb light rather than emit light, they can also be referred to as "spatial light modulators."

For example, the variable transparency layer may vary its opacity when a voltage is applied via polymer dispersed liquid crystal (PDLC) technology. Voltage can be used to change the position and orientation of liquid crystals disposed within a polymer matrix in order to allow more or less light to pass through the variable transparency layer. In such embodiments, the variable transparency layer can include electrically-conductive coatings (e.g., polyethylene terephthalate (PET)) on each side of a polymer matrix that includes randomly-arranged liquid crystals. When the power component 702 applies a voltage to the conductive coatings, the liquid crystals within the polymer matrix become aligned and the variable transparency layer becomes substantially or entirely transparent. However, when the power component 702 ceases to apply the voltage, the liquid crystals scatter and the variable transparency layer becomes substantially opaque or translucent.

As another example, the variable transparency layer may darken its appearance when a voltage is applied via electrochromism. Electrochromism enables some materials to reversible change opacity by using bursts of voltage to cause electrochemical redox reactions in electrochromic materials. In such embodiments, the variable transparency layer may include a first conducting oxide layer, an electrochromic layer (e.g., tungsten oxide ($WO_3$)), an ion conductor layer, an ion storage layer (e.g., lithium cobalt oxide ($LiCoO_2$)), and a second conducting oxide layer. The conducting oxide layers may be thin films of optically-transparent, electrically-conductive materials, such as indium tin oxide (ITO). The conducting oxide layers could also be composed of other transparent conductive oxides (TCOs), conductive polymers, metal grids, carbon nanotubes, graphene, ultrathin metal films, or some combination thereof. The ion conductor layer can include a liquid electrolyte or a solid (e.g., inorganic or organic) electrolyte. In such embodiments, the power component 702 (which is coupled to the conducting oxide layers) is able to selectively apply a voltage to either of the conducting oxide layers, which drives ions from the ion storage layer into the electrochromic layer and vice versa. An ion-soaked electrochromatic layer is able to reflect light, thereby enabling the variable transparency layer to appear at least partially opaque.

Electrochromic and PDLC techniques have been selected for the purpose of illustration. Other technologies that enable the modification of light transmission properties could also be used to achieve the same (or similar) effects, such as photochromic, thermochromic, suspended particle, and micro-blind techniques.

Figure 8:
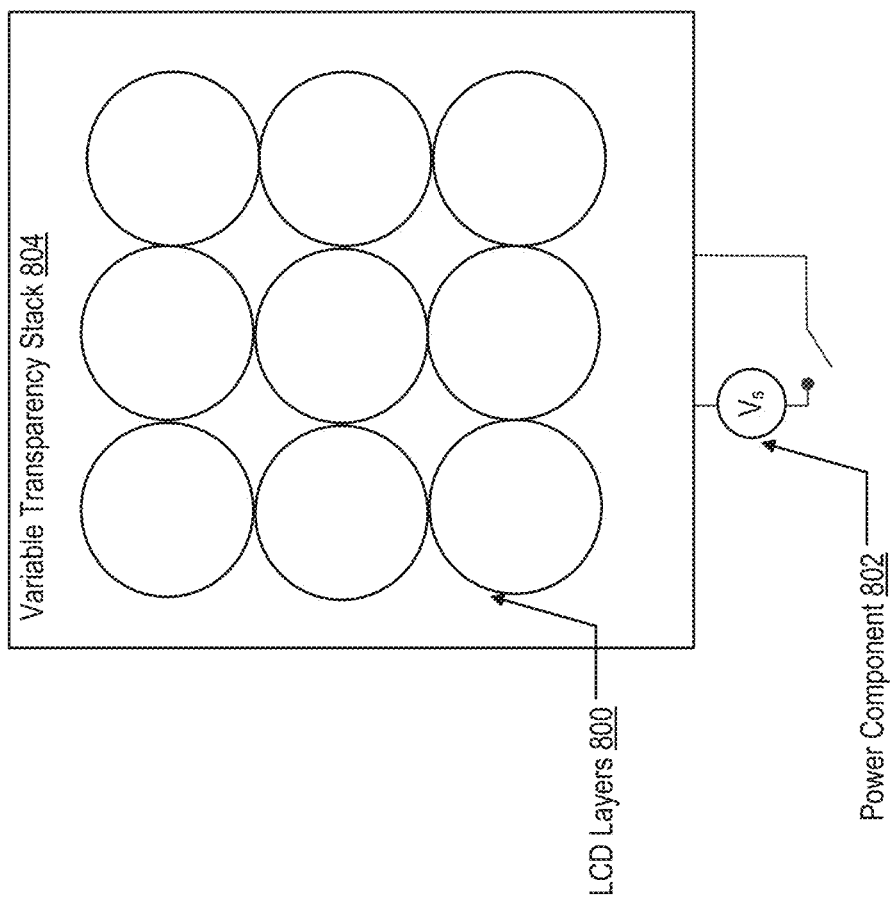
FIG. 8 depicts a variable transparency stack having multiple LCD layers that are individually controllable.

FIG. 8 depicts a variable transparency stack 804 having multiple LCD layers 800 that are individually controllable. As shown in FIG. 7, a single transparent LCD layer may have a periodic pattern that causes it to be pixelated. For example, a substrate (e.g., ITO) may be patterned with a grid of pixels that are separately controllable. However, unlike the pixelated LCD layer 700 of FIG. 7, each LCD layer of the multiple LCD layers 800 included in the variable transparency stack 804 is typically non-pixelated. Here, for example, a substrate (e.g., ITO) is patterned with a geometric shape (e.g., a circle) to form each LCD layer. But rather than pixelate the LCD layers 800, each LCD layer is instead separately connected to the power component 802 (e.g., using separate leads). This ensures that each LED layer can be controlled independently of the other LED layer(s).

The multiple LCD layers 800 can be connected to one another to form the variable transparency stack 804. As shown in FIG. 8, each LCD layer within the variable transparency stack 804 may be offset from the other LCD layers. In some embodiments, each of the LCD layers 800 partially overlaps at least one other LCD layer. The size of the optical stop of the retinal camera can be varied by changing which LCD layer(s) are active at a given point in time. For example, if the bounds of the optical stop are defined by the collective area of multiple LCD layers, then the size of the optical stop can be decreased by deactivating at least one of the multiple LCD layers. Thus, the LCD layers 800 within the variable transparency stack 804 may be lit or unlit depending on the position of the eye being imaged.

The variable transparency stack 804 may include any number of LED layers 800. For example, embodiments may include four, six, eight, or ten LED layers. Moreover, the LED layers 800 within the variable transparency stack 804 may be of the same size and/or shape, or different sizes and/or shapes.

The outer bounds of the variable transparency stack 804 limit the possible positions of the optical stop. The arrangement of the LCD layers 800 (and thus the outer bounds of the variable transparency stack 804) may be based on factors influencing the optical design of the retinal camera as a whole, including the number, type, or placement of lenses (e.g., the lenses 304 of FIG. 3), the expected eye location, etc.

The variable transparency stack 804 can include the multiple LCD layers 800 and other layers (e.g., optically-clear adhesive layers). For example, optically-clear bonding layers may be used to bind the LCD layers 800 to one another. Each bonding layer can include an adhesive (e.g., an acrylic-based adhesive or a silicon-based adhesive). Moreover, each bonding layer is preferably substantially or entirely transparent (e.g., greater than 99% light transmission). The bonding layers may also display good adhesion to a variety of substrates, including glass, ITO, polyethylene (PET), polycarbonate (PC), polymethyl methacrylate (PMMA), etc.

An optical stop unit including the optical stop 302 of FIG. 3, the variable transparency stack 804 of FIG. 8, or the LCD layer 700 of FIG. 7 can be adapted for use within an ophthalmic imaging apparatus. For example, in some embodiments the optical stop unit includes a unit housing designed to fit within the ophthalmic imaging apparatus. Other components (e.g., the power component 702 of FIG. 7 or the power component 802 of FIG. 8) could also reside within the unit housing. Moreover, the optical stop unit may include a communication interface configured to receive a command from a controller of the ophthalmic imaging apparatus, and then select a voltage to apply based on the command. The voltage could cause servomotor(s) to increase/decrease the size of the optical stop 302 of FIG. 3, certain pixel(s) within the LCD layer 700 of FIG. 7 to become transparent, or certain layer(s) within the variable transparency stack 804 of FIG. 8 to become transparent.

FIG. 9 depicts a flow diagram of a process 900 for dynamically modifying the size of an optical stop housed within a retinal camera as a subject shifts their eye before the imaging process. Initially, the subject places an eye proximate to the objective lens of a retinal camera (step 901). The subject will typically sit near the retinal camera with their chin set within a chin rest and their forehead pressed against a bar.

The retinal camera can determine the location of the eye being imaged by the retinal camera (step 902). As noted above, several different mechanisms may be used to establish the location of the eye (and, more specifically, the iris). For example, infrared light source(s) may be configured to project infrared beam(s) into the visible light illumination path of the retinal camera. Because the iris will generally not constrict when illuminated by infrared light, a live view of the retina can be captured and used to establish the position of the eye. As another example, the retinal camera may capture retinal images with the retinal stop located at different positions. Image processing algorithm(s) may be applied to the retinal images to determine whether the retina has been captured in any of the retinal images.

The retinal camera can then configure the optical stop to be a first size (step 903). Generally, the first size is larger than the iris (e.g., 2×, 3×, or 5× larger than the iris). Although such action will ensure that the eye can easily fit within the eyebox, large optical stops are not capable of capturing high-quality images of the retina.

The retinal camera may also monitor the position of the eye (step 904). The retinal camera may use the same tracking mechanism used to initially determine the location of the eye or a different tracking mechanism. For example, the retinal camera may use a higher-resolution tracking mechanism to continually monitor the position of the eye so that small variations (e.g., those less than one millimeter) can be consistently detected.

Responsive to determining that the position of the eye has changed, the retinal camera can adjust the optical stop to be a second size (step 905). For example, as the position of the eye approaches a specified location, the bounds of the optical stop can constrict. As another example, as the position of the eye diverges from the specified location, the bounds of the optical stop can expand. The retinal camera may be configured to automatically expand and/or constrict the bounds of the optical stop until the iris is properly aligned with the specified location. The specified location may be the epicenter of the optical stop.

The size of the optical stop can be set manually or automatically. For example, the retinal camera may instruct servomotor(s) to rotate a series of blades that mechanically define the boundary of the optical stop. As another example, the retinal camera may instruct power component(s) to controllably apply a voltage to a series of LCD pixels that electronically define the boundary of the optical stop. These instructions may be generated responsive to adjustments specified by software executing on the retinal camera or another computing device communicatively coupled to the retinal camera.

The retinal camera can then generate a retinal image from light rays reflected into the retinal camera by the eye (step 906). Such action may be performed responsive to a determination that the size of the optical stop substantially matches the size of the iris. This may require that the size of the optical stop be adjusted several times (e.g., the retinal camera may adjust the size multiple times before substantially matching the size of the iris). Moreover, the retinal camera may be prompted to generate the retinal image by a retinal photographer pressing a shutter release that causes the retinal image to be captured.

Unless contrary to physical possibility, it is envisioned that the steps described above may be performed in various sequences and combinations. For example, the retinal camera may automatically adjust the size of the optical stop each time the position of the eye is modified until the iris is properly aligned with a similarly-sized optical stop. Thus, the optical stop may be automatically resized without requiring input from the retinal photographer or the subject. Instead, the subject may be able to look into the retinal camera without being concerned about alignment of the eye and the optical stop.

Other steps may also be included in some embodiments. For example, the retinal camera could be programmed to generate a series of images within a specified white exposure time (e.g., 150 milliseconds) corresponding to optical stops of different sizes. By examining the clarity of these images, the retinal camera can establish the position of the eye.

Processing System

Figure 10:
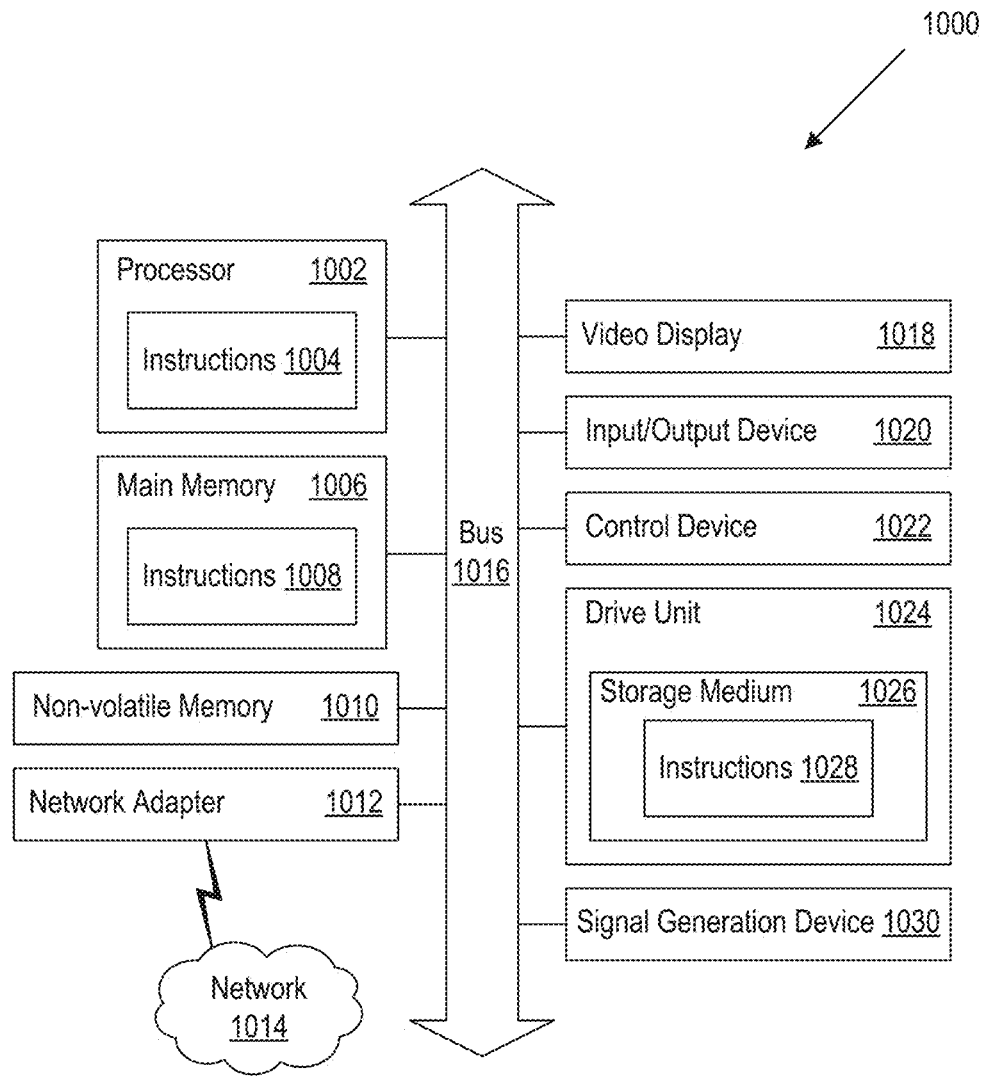
FIG. 10 is a block diagram illustrating an example of a processing system in which at least some operations described herein can be implemented.

FIG. 10 is a block diagram illustrating an example of a processing system 1000 in which at least some operations described herein can be implemented. For example, some components of the processing system 1000 may be hosted on a retinal camera (e.g., retinal camera 300 of FIG. 3), while other components of the processing system 1000 may be hosted on a computing device that is communicatively coupled to the retinal camera. The computing device may be connected to the retinal camera via a wired channel or a wireless channel.

The processing system 1000 may include one or more central processing units ("processors") 1002, main memory 1006, non-volatile memory 1010, network adapter 1012 (e.g., network interface), video display 1018, input/output devices 1020, control device 1022 (e.g., keyboard and pointing devices), drive unit 1024 including a storage medium 1026, and signal generation device 1030 that are communicatively connected to a bus 1016. The bus 1016 is illustrated as an abstraction that represents one or more physical buses and/or point-to-point connections that are connected by appropriate bridges, adapters, or controllers. The bus 1016, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1000 may share a similar computer processor architecture as that of a desktop computer, tablet computer, personal digital assistant (PDA), mobile phone, game console, music player, wearable electronic device (e.g., a watch or fitness band), network-connected ("smart") device (e.g., a television or home assistant device), virtual/augmented reality system (e.g., a head-mounted display), or another electronic device capable of executing a set of instructions (sequential or otherwise) that specify action(s) to be taken by the processing system 1000.

While the main memory 1006, non-volatile memory 1010, and storage medium 1026 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1028. The term "machine-readable medium" and "storage medium" shall also be taken to include any medium that is capable of storing, encoding, or carrying a set of instructions for execution by the processing system 1000.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1004, 1008, 1028) set at various times in various memory and storage devices in a computing device. When read and executed by the one or more processors 1002, the instruction(s) cause the processing system 1000 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1010, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1012 enables the processing system 1000 to mediate data in a network 1014 with an entity that is external to the processing system 1000 through any communication protocol supported by the processing system 1000 and the external entity. The network adapter 1012 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1012 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A non-transitory computer-readable medium with instructions stored thereon that, when executed by a processor, cause the processor to perform operations comprising:
configuring an optical stop that collects light to image an eye of an individual to be a first size;
identifying a first location of the eye to be imaged by an imaging apparatus to which the individual presents the eye for examination;
monitoring for a spatial adjustment of the eye along a plane that causes the eye to be located at a second location,
wherein the plane is substantially orthogonal to a path along which the light is directed toward the optical stop;
determining that the second location differs from the first location; and
adjusting the optical stop to be a second size based on the second location.

2. The non-transitory computer-readable medium of claim 1, wherein the spatial adjustment is prompted by vignetting of an image visible to the eye through the imaging apparatus, and wherein the vignetting is caused by the first size being at least two times larger than an iris of the eye.

3. The non-transitory computer-readable medium of claim 2,
wherein continual performance of the operations facilitates alignment of the eye and an epicenter of the optical stop prior to initiation of an imaging process, and
wherein said adjusting lessens vignetting visible to the eye through the imaging apparatus.

4. The non-transitory computer-readable medium of claim 3, wherein said adjusting results in an improvement in quality by improving resolution, improving brightness, or eliminating vignetting.

5. The non-transitory computer-readable medium of claim 1,
wherein the spatial adjustment causes the eye to be located closer to a specified location that aligns with an epicenter of the optical stop, thereby improving alignment of a retina and the optical stop, and
wherein the second size is smaller than the first size.

6. The non-transitory computer-readable medium of claim 1,
wherein the spatial adjustment causes the eye to be located further from a specified location that aligns with an epicenter of the optical stop, thereby worsening alignment of a retina and the optical stop, and
wherein the second size is larger than the first size.

7. The non-transitory computer-readable medium of claim 1, wherein the operations further comprise:
generating an image to be shown to the eye.

8. The non-transitory computer-readable medium of claim 7, wherein spatial adjustments of the eye toward a specified location that aligns with an epicenter of the optical stop improve clarity of the image.

9. The non-transitory computer-readable medium of claim 1, wherein the operations further comprise:
monitoring for another spatial adjustment of the eye along the plane that causes the eye to be located at a third location;
determining that the third location differs from the second location; and
adjusting the optical stop to be a third size based on the third location.

10. The non-transitory computer-readable medium of claim 9,
wherein the other spatial adjustment causes the eye to be located closer to a specified location that aligns with an epicenter of the optical stop, thereby improving alignment of a retina and the optical stop, and
wherein the third size is smaller than the second size.

11. The non-transitory computer-readable medium of claim 9,
wherein the other spatial adjustment causes the eye to be located further from a specified location that aligns with an epicenter of the optical stop, thereby worsening alignment of a retina and the optical stop, and
wherein the third size is larger than the second size.

12. The non-transitory computer-readable medium of claim 1, wherein said identifying, said monitoring, said determining, and said adjusting are performed iteratively until the optical stop is a predetermined size.

13. The non-transitory computer-readable medium of claim 1, wherein a difference between the first and second sizes is based on a diameter of an iris of the eye.

14. The non-transitory computer-readable medium of claim 13, wherein the difference between the first and second sizes is based on magnification of the iris.

15. The non-transitory computer-readable medium of claim 1, wherein the second size is substantially identical to a diameter of an iris of the eye after accounting for magnification.

* * * * *